(12) United States Patent
Litke et al.

(10) Patent No.: US 12,137,936 B2
(45) Date of Patent: Nov. 12, 2024

(54) MULTIPLE PORT INSTRUMENT ACCESS DEVICE

(71) Applicant: Intuitive Surgical Operations, Inc., Sunnyvale, CA (US)

(72) Inventors: Ronald G. Litke, Sandy Hook, CT (US); Kyle Miller, San Jose, CA (US); Jake A. Luckman, New Haven, CT (US); Joseph P. Orban, III, Norwalk, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/391,484

(22) Filed: Dec. 20, 2023

(65) Prior Publication Data

US 2024/0206910 A1 Jun. 27, 2024

Related U.S. Application Data

(63) Continuation of application No. 17/180,382, filed on Feb. 19, 2021, now Pat. No. 11,883,066.
(Continued)

(51) Int. Cl.
*A61B 17/34* (2006.01)
*A61B 17/02* (2006.01)
(Continued)

(52) U.S. Cl.
CPC .......... *A61B 17/3423* (2013.01); *A61B 17/02* (2013.01); *A61B 34/35* (2016.02); *A61M 13/003* (2013.01); *A61B 2017/3441* (2013.01)

(58) Field of Classification Search
CPC . A61B 17/02; A61B 17/0218; A61B 17/3421; A61B 17/3423; A61B 17/3431; A61B 17/3439; A61B 17/3462; A61B 2017/0225; A61B 2017/3425; A61B 2017/3427; A61B 2017/3429; A61B 2017/3433; A61B 2017/3441;
(Continued)

(56) References Cited

U.S. PATENT DOCUMENTS 5,653,705 A * 8/1997 de la Torre ........ A61B 17/3462
606/1
8,920,431 B2 * 12/2014 Shibley ..................... A61J 1/10
606/114

(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Eric S Gibson
(74) *Attorney, Agent, or Firm* — Schwegman, Lundberg & Woessner, P.A.

(57) ABSTRACT

An instrument access device of a teleoperated surgical system includes an envelope, a clamp, and a plurality of ports. The envelope includes a distal opening and a cavity. The clamp is in the distal opening of the envelope. The plurality of ports are coupled to the envelope. The plurality of ports are proximal to the clamp and the distal opening of the envelope. Each of the plurality of ports includes a seal, which is sized and shaped to seal an outer surface of a cannula and to fix a position of the cannula relative to the port and the envelope.

20 Claims, 12 Drawing Sheets

Related U.S. Application Data

(60) Provisional application No. 62/978,693, filed on Feb. 19, 2020.

(51) Int. Cl.
   *A61B 34/35* (2016.01)
   *A61M 13/00* (2006.01)

(58) Field of Classification Search
   CPC .... A61B 2017/3443; A61B 2017/3445; A61B 2017/3447; A61B 2017/3449; A61B 2017/3466
   See application file for complete search history.

(56) References Cited

U.S. PATENT DOCUMENTS

| | | | |
|---|---|---|---|
| 10,201,371 B2* | 2/2019 | Cahill | A61M 13/00 |
| 11,883,066 B2* | 1/2024 | Litke | A61B 17/3423 |
| 2002/0038077 A1* | 3/2002 | de la Torre | A61B 46/10 |
| | | | 600/203 |
| 2005/0137609 A1* | 6/2005 | Guiraudon | A61B 17/3423 |
| | | | 606/108 |
| 2008/0255519 A1* | 10/2008 | Piskun | A61B 17/3439 |
| | | | 600/109 |
| 2009/0187079 A1* | 7/2009 | Albrecht | A61B 1/32 |
| | | | 600/184 |
| 2010/0081882 A1* | 4/2010 | Hess | A61B 17/3423 |
| | | | 600/245 |
| 2010/0094227 A1* | 4/2010 | Albrecht | A61B 17/3421 |
| | | | 604/167.01 |
| 2010/0174143 A1* | 7/2010 | Abrams | A61B 17/3462 |
| | | | 600/121 |
| 2010/0249694 A1* | 9/2010 | Choi | A61B 17/0293 |
| | | | 604/167.03 |
| 2011/0011410 A1* | 1/2011 | Desai | A61B 17/3423 |
| | | | 128/898 |
| 2012/0022333 A1* | 1/2012 | Main | A61B 17/3462 |
| | | | 600/201 |
| 2013/0324800 A1* | 12/2013 | Cahill | A61B 17/3423 |
| | | | 600/204 |
| 2015/0238179 A1* | 8/2015 | Kanehira | A61B 17/0293 |
| | | | 600/204 |
| 2018/0214681 A1* | 8/2018 | Crews | A61B 17/3423 |
| 2018/0338777 A1* | 11/2018 | Bonadio | A61M 13/003 |
| 2019/0117209 A1* | 4/2019 | Augelli | A61B 17/3423 |
| 2019/0117255 A1* | 4/2019 | Kleyman | A61B 17/3474 |
| 2021/0251655 A1* | 8/2021 | Litke | A61B 90/40 |

* cited by examiner

MULTIPLE PORT INSTRUMENT ACCESS DEVICE

CLAIM OF PRIORITY

This application is a continuation of and claims the benefit of priority under 35 U.S.C. § 120 to U.S. patent application Ser. No. 17/180,382, filed on Feb. 19, 2021, which claims the benefit of priority under 35 U.S.C. § 119(e) to U.S. Patent Application Ser. No. 62/978,693, filed on Feb. 19, 2020, each of which is incorporated by reference herein in its entirety.

TECHNICAL FIELD

This document relates generally to medical devices, and more particularly, to devices and methods for providing teleoperated surgical instruments access to a surgical site.

BACKGROUND

Surgical systems, such as those employed for minimally invasive medical procedures, can include large and complex equipment to precisely control and drive relatively small tools or instruments. Such systems are sometimes referred to as a teleoperated systems or a robotic surgical systems. One example of a teleoperated surgical system is the da Vinci® Surgical System commercialized by Intuitive Surgical, Inc.

Teleoperated systems can control and drive multiple instruments through multiple access ports in the body of the patient. Additionally, some teleoperated systems are configured to deliver multiple instruments through a single access port in the body of the patient by employing an instrument entry guide that includes multiple channels to accommodate the multiple instruments.

The access ports through which teleoperated systems deliver instruments to the body are typically sealed to maintain insufflation flow and pressure during the surgical procedure. In some cases, an access port device, which may include, for example, a wound retractor, a cannula received in the wound and wound retractor, and an entry guide received in the cannula, is disposed at the site of incision in the body of the patient. The seals that maintain insufflation pressure are included in the access port device and are thereby also located generally adjacent to the incision/surface of the body. In such situations, articulation of the instruments of the teleoperated system occurs just outside and above the incision site and the instrument end effectors are located inside the body below the incision and the outer surface of the body.

The end effectors that are manipulated by the surgeon in these types of procedures are located relatively deeply within the body of the patient. There are situations, however, where it may be necessary or advantageous to control the end effectors of the instruments at or very close to the surface of the body at the incision site. In such situations, the challenge is maintaining insufflation of the body cavity of the patient while also providing enough room for the arms of the instruments to articulate outside the body such that the instrument end effectors are located at or near the surface of the body.

SUMMARY

An instrument access device of a teleoperated surgical system includes an envelope, a clamp, and a plurality of ports. The envelope includes a distal opening and a cavity. The clamp is in the distal opening of the envelope. The plurality of ports are coupled to the envelope. The plurality of ports are proximal to the clamp and the distal opening of the envelope. Each of the plurality of ports includes a seal, which is sized and shaped to seal an outer surface of a cannula and to fix a position of the cannula relative to the port and the envelope.

Another example instrument access device includes means for enclosing a cavity, means for connecting the means for enclosing to a wound retractor, and means for sealing each of a plurality of cannulas. The means for sealing is connected to the means for enclosing. And, the means for sealing is configured to fix a position of each of the plurality of cannulas relative to the means for enclosing.

Each of these non-limiting examples can stand on its own or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about various aspects of the inventive subject matter of the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
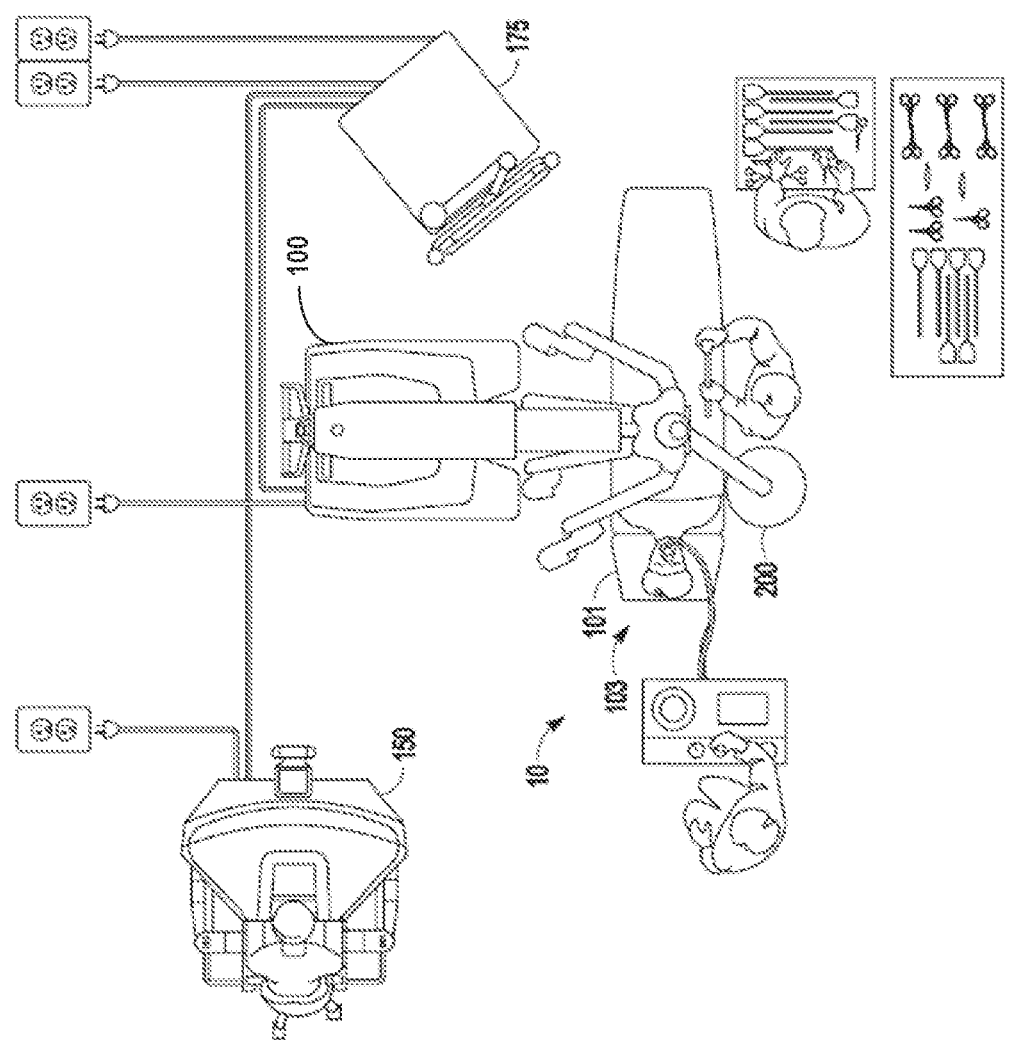
FIG. 1A is a plan view illustration of an example medical system in a surgical environment.

Examples according to this disclosure include an instrument access device that includes an envelope including a distal opening and a cavity. A clamp is positioned in the distal opening of the envelope and the clamp can be coupled to a wound retractor. A plurality of ports are coupled to the envelope. The plurality of ports are proximal to the clamp and the distal opening of the envelope. Each port includes a cannula seal. The seal is sized and shaped to seal an outer surface of a cannula and to fix a position of the cannula relative to the port and the envelope. The instrument access device is configured to receive an insufflation gas and to maintain insufflation pressure within a cavity in the body of a patient and to maintain insufflation pressure within the cavity of the envelope. The pressurized and sealed envelope cavity provides an operating space for arms/shafts of multiple instruments of a teleoperated surgical system to articulate outside the body such that instrument end effectors are located at or near the surface of the body at the incision site of the wound retractor coupled to the instrument access device.

In some examples, the seal of each of the access ports includes a pair of seals. A duck bill or cross-slit seal seals the instrument or cannula (in which an instrument is received) and the port for insufflation gas pressure. An O-ring seal serves two purposes. It seals the port for insufflation gas and it serves to hold the instrument or cannula in a fixed position relative to the port.

In some examples, the envelope of the instrument access device includes a plurality of ports that number greater than the number of associated instrument shafts and end effectors of the teleoperated surgical system. For example, the envelope of the instrument access device may include a first plurality of ports. The first plurality of ports are equal in number to the number of instrument shafts and end effectors of the teleoperated surgical system and are located on the envelope in accordance with a first type of surgical procedure. The envelope also includes a second plurality of ports. The second plurality of ports are equal in number to the number of instrument shafts and end effectors of the teleoperated surgical system and are located on the envelope in accordance with a second type of surgical procedure.

For minimally invasive surgery, the instruments (or, more generally, end effectors) of the teleoperated surgical system must remain substantially stationary with respect to the location at which the instruments enter the patient's body, either at an incision or at a natural orifice, to avoid unnecessary tissue damage. Accordingly, the yaw and pitch motions of the instruments should be centered around a single location on a manipulator assembly roll axis that stays relatively stationary in space. This location is referred to as remote center of motion. The remote center of motion is the location at which yaw, pitch, and roll axes of the manipulator assembly intersect (i.e., the location at which the kinematic chain of the manipulator assembly remains effectively stationary while joints move through their range of motion). In examples according to this disclosure, a flexible envelope including multiple ports enables locating the articulation of end effectors outside or less deep within the body of the patient. The ability to position the end effectors in this manner allows the surgeon to move the remote center of operation of the teleoperated system arms without impacting the incision or skin of patient, which can, under some circumstances, decrease negative effects on patient tissue and increase surgical flexibility for the surgeon.

FIG. 1A is a plan view depicting an example medical procedure environment that includes a multi-arm manipulating system 100 adjacent to a surgical table 101 that supports a patient 103. A second manipulating system 200 may also be situated at the surgical table 101. The manipulating systems 100, 200 may be free-standing on a movable base, or they may be mounted to a table, floor, wall, or ceiling, or they may be supported on another piece of equipment in the clinical environment.

The manipulating system 100 or system 200 may be part of a larger system 10, which may include other sub-systems, including, for example, fluoroscopy or other imaging equipment. One or both of the manipulating systems 100, 200 may be operatively coupled to a user control system 150 or an auxiliary system 175, or both. The user control system 150 may include one or more user input devices (e.g., controls) that may be configured to receive inputs from a user (e.g., clinician). The user control system 150 may also include or one or more user feedback devices (e.g., viewing system, or tactile or auditory feedback system) that may be configured to provide information to the user regarding the movement or position of an end effector, or an image of a surgical area. The auxiliary system 175 may, for example, include computer processing equipment (e.g., a processor circuit or graphics hardware), or communication equipment (e.g., wired or wireless communication circuits), or endoscopic camera control and image processing equipment.

Figure 1B:
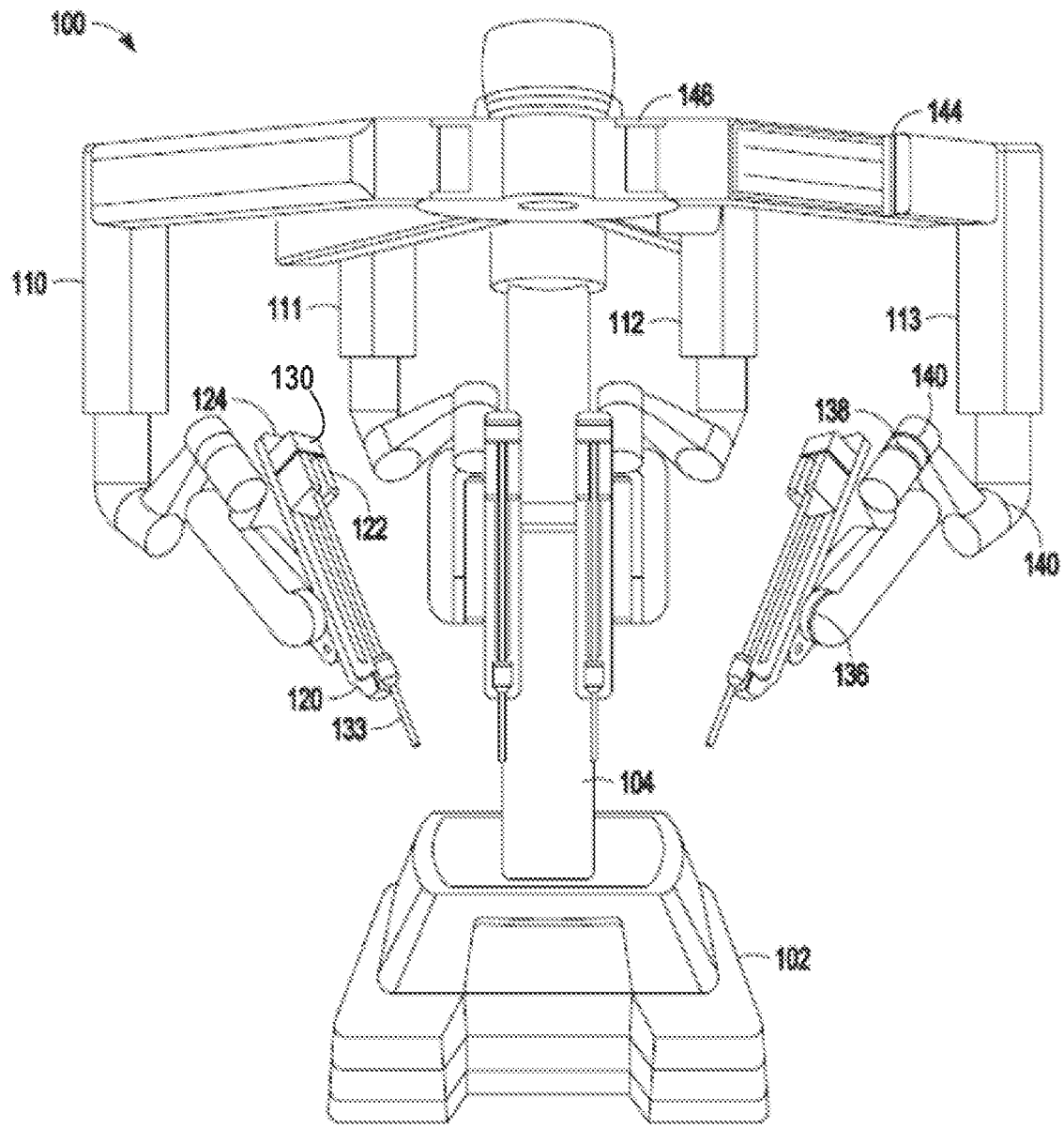
FIG. 1B is an illustration of an example manipulating system.

FIG. 1B depicts example manipulating system 100. The example manipulating system 100 includes a base 102, a support tower 104, and one or more manipulator arms 110, 111, 112, 113, which may be mounted on the support tower 104. An instrument 130 (shown in more detail in FIG. 1E) is mounted to an instrument mount 120 on one of the manipulator arms 110-113. The instrument mount 120 includes, as an example, an instrument carriage 122, which is mounted to a spar 124, which may be a telescoping or non-telescoping spar. A cannula 133 may be mounted to a cannula mount 126, and the instrument 130 may be inserted through a cannula seal in the cannula 133, and into the patient 103 (FIG. 1A) for use in a therapeutic or diagnostic surgical procedure. Through movement of the manipulator arms 110-113, the translation and orientation of the instrument 130 may be controlled in multiple mechanical degrees of freedom, e.g. lateral, horizontal, vertical, angular movements in one, two, or three planes. The system 100 may include one or more light features 136, 138, 140, 142, 144, 146 at one or more of a variety of locations on the manipulator arms 110-113 (i.e., at joints between arm links, as shown).

Cannula 133 may be inserted into the patient 103, and a surgical instrument seal assembly (not shown) is inserted into the cannula. The instrument seal prevents insufflation gas from escaping through the open cannula when no instrument is inserted in the cannula, and it also prevents insufflation gas from escaping between the instrument shaft and the cannula inner wall when an instrument is inserted in the cannula.

Figure 1C:
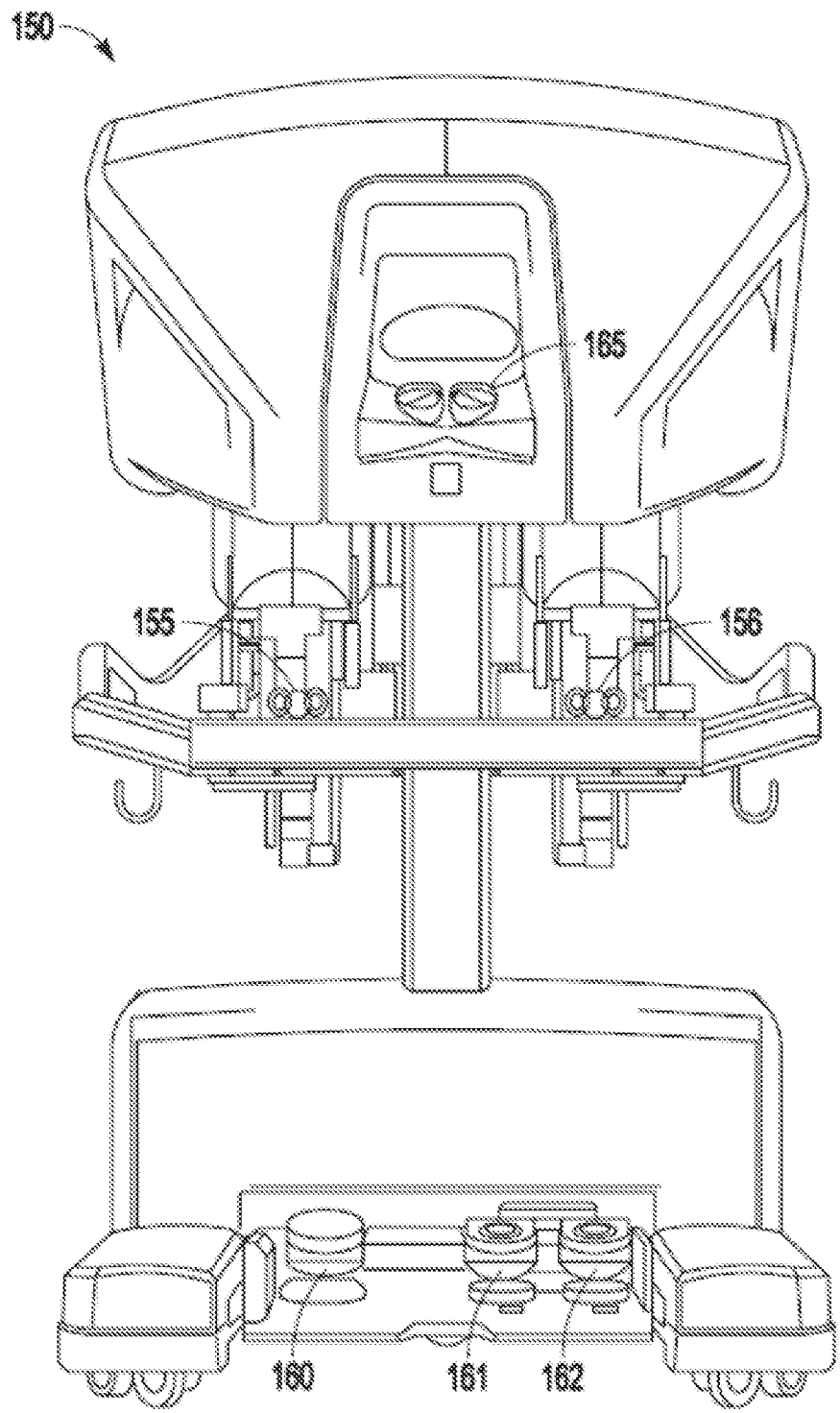
FIG. 1C is an illustration of an example user control system.

FIG. 1C depicts example user control system 150. The user control system 150 includes hand controls 155, 156 and foot pedal controls 160, 161, 162. The hand controls 155, 156 and foot pedal controls 160, 161, 162 are used to control equipment at one or more of the manipulating systems 100, 200. For example, an operator may manipulate portions of a distal end of an instrument 130 by using the instrument controls. The controls may include haptic feedback features so that a surgeon may interpret physical information at the instrument 130, such as resistance or vibration, through the controls. The user control system 150 may also include a viewing system 165 that displays video or other images of a surgical site.

Figure 1D:
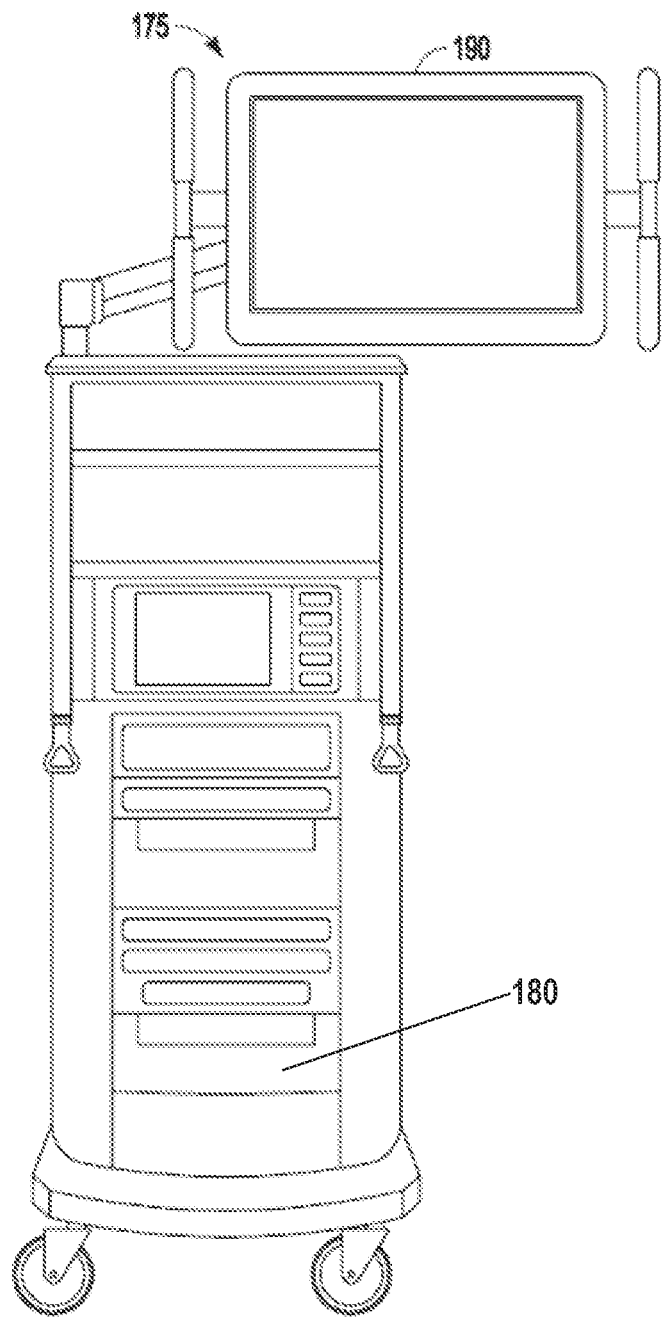
FIG. 1D is an illustration of an example auxiliary system.

FIG. 1D depicts an example auxiliary system 175. The example auxiliary system 175 optionally includes telesurgical system functions that are not incorporated into other system units, such as computer processing system 180 for processing teleoperation controls, facilitating communication between the user control system and the manipulating system, or a remote site, endoscopic camera control and illumination, electrosurgical generation and control, etc. The auxiliary system 175 may also include a display 190, which shows images that the user (e.g., a clinician) is seeing on the user control system 150, a video feed from a camera in the patient 103, or other information. In an example configuration, signals input at a user control system 150 may be transmitted to the processing system 180 on the auxiliary system 175, which interprets the inputs and generate commands that are transmitted to the manipulating system 100 to cause manipulation of an instrument 130 or portions of a manipulator arm 110. The processing system 180 is shown on a cart for exemplary purposes, but it may also be arranged in various configurations, e.g., it may be integrated as part of the user control system 150, the manipulating system 100, 200, or both, or divided between the user control system 150 and manipulating system 100, 200. The equipment may also be provided as software, hardware, or both, on an installed or remote system.

Figure 1E:
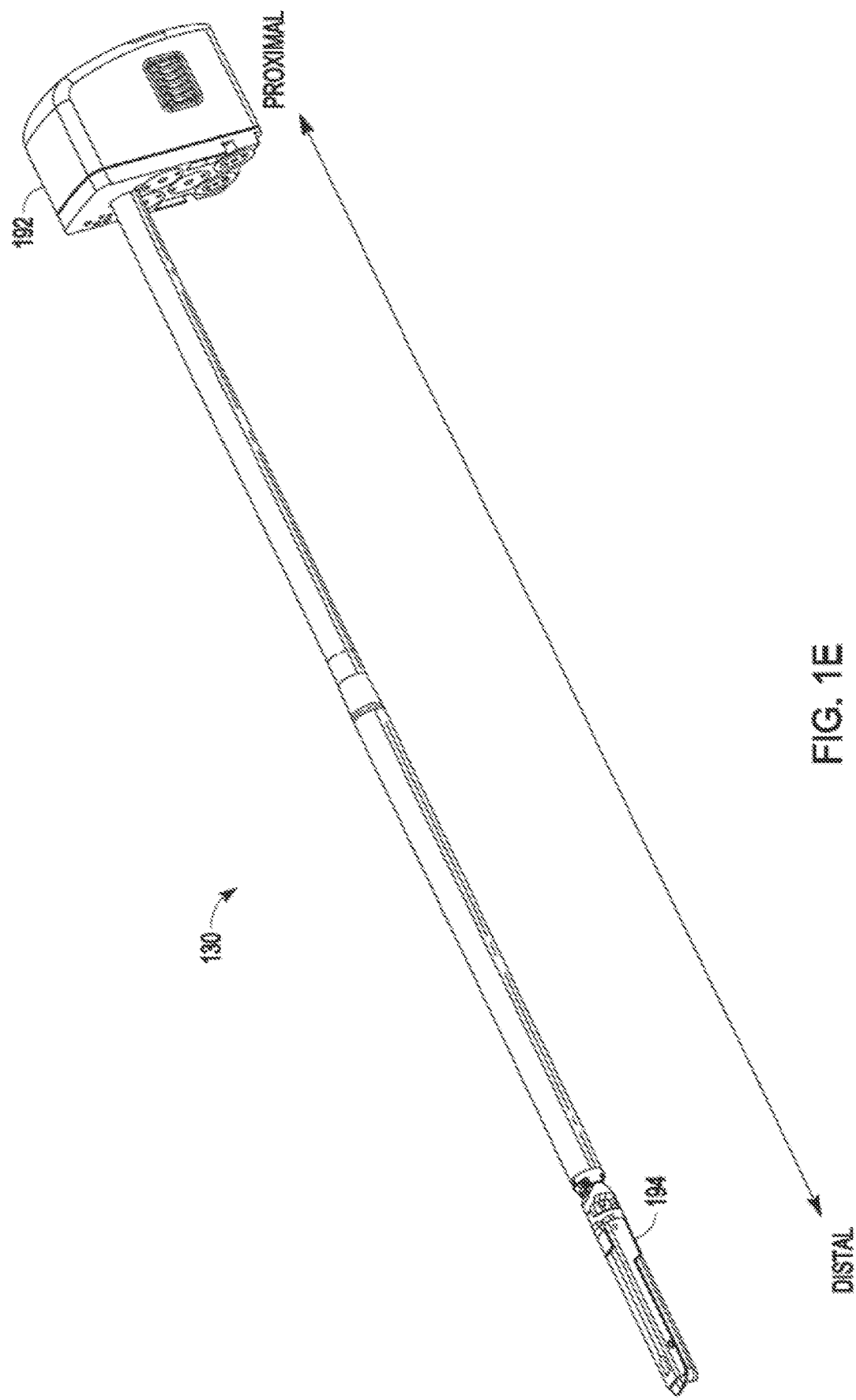
FIG. 1E is an illustration of an example instrument.

FIG. 1E depicts example instrument 130. The instrument 130 includes a proximal portion 192, which is configured to couple to an instrument mount on a manipulator arm. The instrument 130 also includes a distal portion 194 and an instrument shaft 196 between the proximal portion 192 and the distal portion 194. The distal portion 194 shown is a stapler, and in other instruments it may be a cautery tool, cutter, camera, or other medically relevant end effector. The instrument 130 may be teleoperatively controlled via command signals received from a control computer, such as a user control system 150 or auxiliary system 175 to conduct a surgical procedure. Inputs may be received from a user (e.g., clinician), and the instrument 130 may be controlled based on the user inputs.

In an example, instrument 130 is inserted into the patient 130 via cannula 133, which also contains a surgical instrument seal assembly as described above. In such a procedure, it may be important to provide and maintain insufflation of a body cavity of the patient 130.

Figure 2:
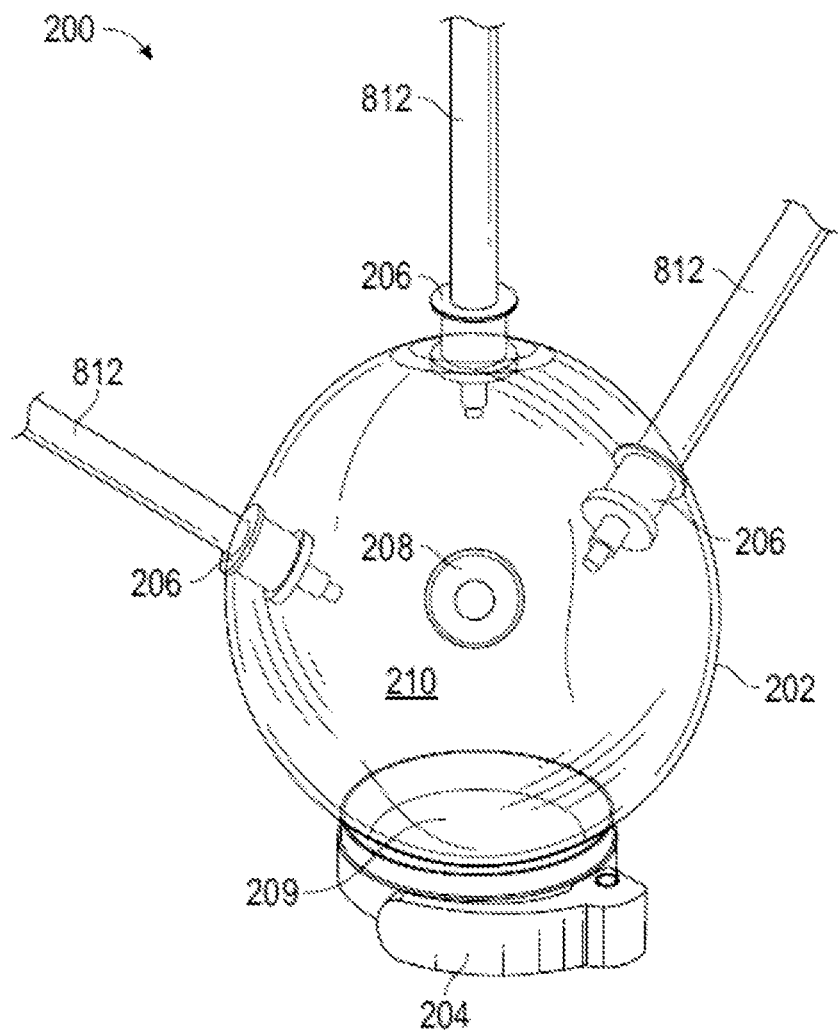
FIG. 2 is a perspective view depicting an example instrument access device in accordance with this disclosure.

FIG. 2 is a perspective view depicting instrument access device 200 in accordance with this disclosure. Instrument access device 200 includes envelope 202, clamp 204, ports 206, and assistant port 208. Envelope 202 includes distal opening 209 and cavity 210. Clamp 204 is located in distal opening 209 of envelope 202. Clamp 204 can be connected to distal opening 209 of envelope 202 by a variety of means, including using an adhesive or heat-sealing envelope 202 to clamp 204. Ports 206 and assistant port 208 are coupled to envelope 202. Additionally, ports 206 and assistant port 208 are proximal to clamp 204 and distal opening 209 of envelope 202.

Instrument access device 200 is configured to receive an insufflation gas and to maintain insufflation pressure within a cavity in the body of a patient and to maintain insufflation pressure within cavity 210 of envelope 202. The pressurized and sealed envelope cavity 210 is configured to allow arms/shafts of multiple instruments to triangulate within cavity 210 of envelope 202. Thus, envelope 202 needs to provide enough space to allow multiple instruments to be manipulated within cavity 210 and to allow a surgeon to triangulate the instruments to perform various procedures at or near the surface of the body at the incision site of a wound retractor coupled to instrument access device 200 at clamp 204.

The pressurized envelope can be manufactured from a transparent material, including, for example, a transparent polymer. As such, envelope 202 provides visualization for the surgeon to see the incision site to which envelope 202 and clamp 204 are connected. Envelope 202 can provide visualization for the surgeon for both cannula ports 206 and assistant port 208 included in instrument access device 200. In addition to being transparent, envelope 202 may also be flexible and cable of being distorted or otherwise deflected from its fully inflated shape. This allows a surgeon to more easily move instrument shafts of the teleoperated surgical system to properly position the instruments/end effectors of such shafts relative to the incision site.

In an example, envelope 202 is manufactured from a thermoplastic polyurethane (TPU). In another example, envelope 202 can be manufactured from various polymer films, including, for example, polyethylene, polypropylene, vinyl, nylon, and/or polyester, among other example materials. Envelope 202 can be manufactured in a variety of ways, including vacuum forming. In another example, envelope 202 is manufactured from a flat panel with multiple seams, which are joined to one another to form the final shape of envelope 202.

As depicted in FIG. 2, each of ports 206 receive one cannula 212, through which an associated instrument of a teleoperated surgical system may be inserted. As will be described in more detail below, each of ports 206 includes a seal (not shown in FIG. 2, see FIG. 3A). The seal in each of ports 206 is sized and shaped to seal an outer surface of one of cannulas 212 and to fix a position of cannula 212 relative to port 206 and envelope 202. In some examples, ports 206 may receive instruments of a teleoperated surgical system directly, i.e. without the use of separate cannulas.

The example of FIG. 2 includes three cannula ports 206 and one assistant port 208. However, in other examples in accordance with this disclosure a different arrangement could be used. For example, an instrument access device can include two or four cannula ports and one or more assistant ports. Commonly, the instrument access device will include three cannula ports, and one assistant port for a manually operated instrument. Of the three cannula ports, one may receive an instrument shaft including a camera at the distal tip and the remaining two may receive two other instrument shafts each with one of various types of instruments like a stapler, cautery tool, or cutter.

Figure 3:
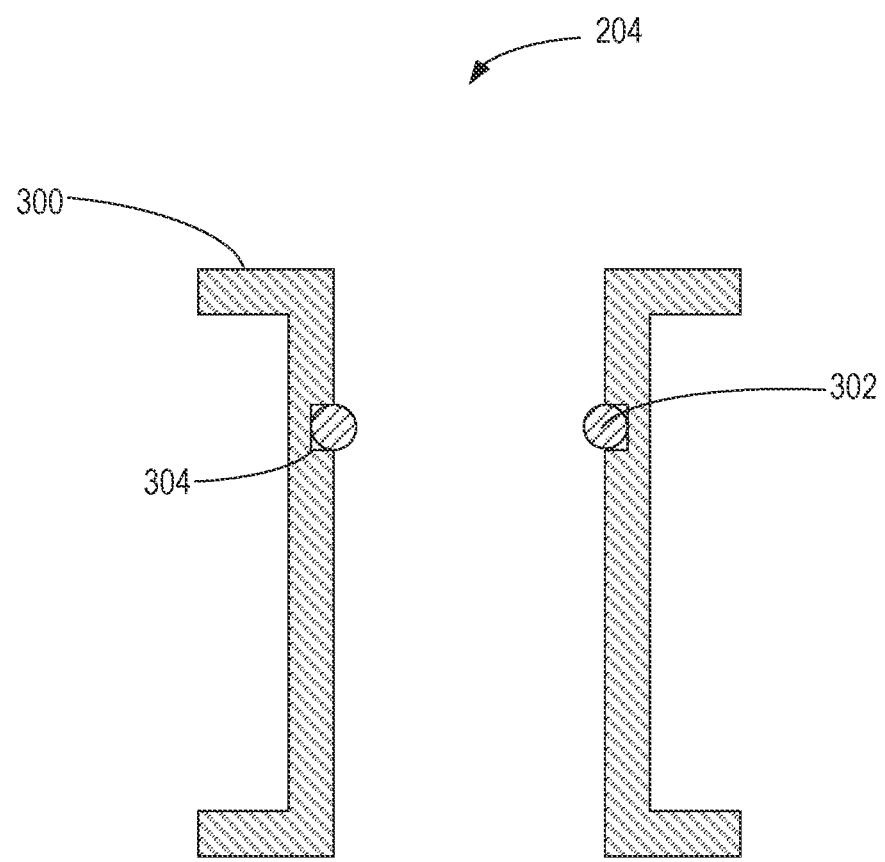
FIG. 3 is a section view schematically depicting one of the ports of the instrument access device of FIG. 1.

FIG. 3 is a section view schematically depicting one of ports 204 of instrument access device 200 of FIG. 1. In FIG. 3, port 204 includes port body 300 and seal 302. Seal 302 is captured at least partially within channel 304 in an inner surface of port body 300. In an example, seal 302 is an O-ring seal. Seal 302 is sized and shaped to seal an outer surface of a of cannula and to fix a position of the cannula relative to port body 300 and relative to an envelope (e.g., envelope 202) to which port body 300 is connected. For example, the inner diameter of seal 302 can be undersized relative to the outer diameter of the cannula received by seal 302 such that the cannula is press-fit into seal 302. The cannula press-fit in seal 302 will serve to seal the outer surface of the cannula and to fix the position of the cannula relative to seal body 300 and relative to the envelope to which seal body 300 is connected.

In practice, a surgeon may insert a cannula into port body 300 and through seal 302 by holding port body 300 and press-fitting the cannula through seal 302. The surgeon may adjust the position of the cannula relative to port body 300 until in a satisfactory position. Thereafter, because seal 302 fixes the position of the cannula relative the cannula relative to seal body 300 and relative to the envelope to which seal body 300 is connected, the surgeon may articulate a surgical instrument received through the cannula without causing the cannula to slide in and out through port body 300 and seal 302.

Figure 4:
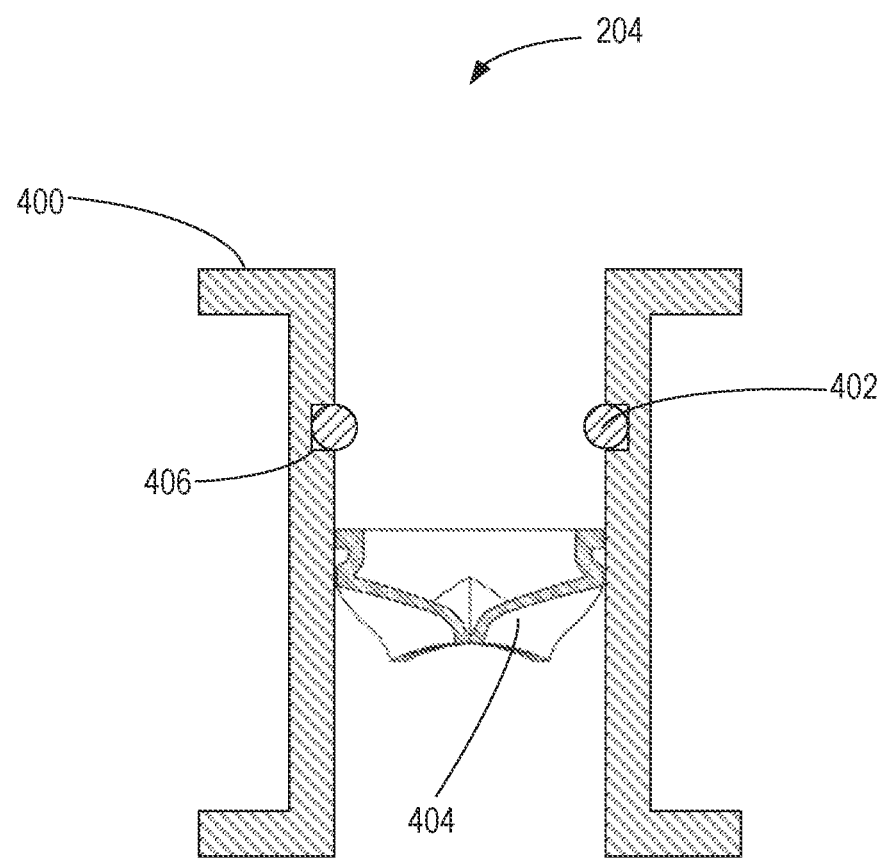
FIG. 4 is a section view schematically depicting an alternative example of one of the ports of the instrument access device of FIG. 1.

FIG. 4 is a section view schematically depicting an alternative example of one of ports 204 of instrument access device 200 of FIG. 1. In FIG. 4, port 204 includes port body 400, first seal 402, and second seal 404. First seal 402 is captured at least partially within channel 404 in an inner surface of port body 400. In an example, first seal 402 is an O-ring seal. First seal 402 is sized and shaped to seal an outer surface of a of cannula and to fix a position of the cannula relative to port body 400 and relative to an envelope (e.g., envelope 202) to which port body 400 is connected. As with the example of FIG. 3, the inner diameter of first seal 402 can be undersized relative to the outer diameter of the cannula received by first seal 402 such that the cannula is press-fit into first seal 402. The cannula press-fit in first seal 402 will serve to seal the outer surface of the cannula and to fix the position of the cannula relative to seal body 400 and relative to the envelope to which seal body 400 is connected.

In the example of FIG. 4, port 204 also includes second seal 404. Second seal 404 is cross-slit seal, which includes a concave distal surface. In other examples, a second seal of a port in accordance with this disclosure could be another type of slit-seal, including a single or three-slit seal. Additionally, the second seal could include other types of seals including a duck bill, wiper, and/or septum seal. Second seal 404 is disposed within port body 400 and configured to seal to the outer surface of the cannula received in the port body. Additionally, second seal 404 is configured to seal the envelope on condition that a cannula is not received through port 204. Thus, second seal 404 serves to seal the instrument access device including the envelope for insufflation gas before a cannula has been received in port 204 or after a cannula has been removed from port 204 during a surgical procedure.

Figure 5:
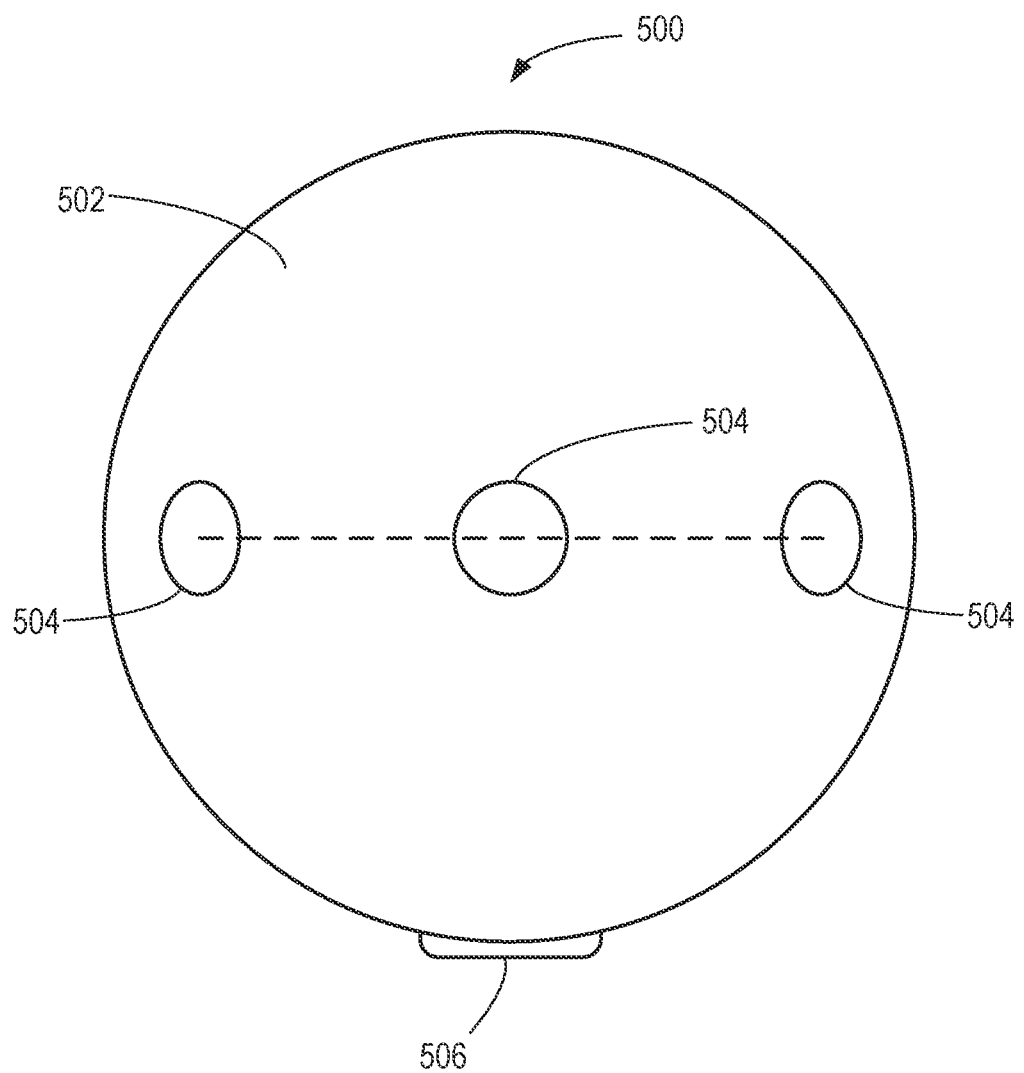
FIG. 5 is a plan view schematically depicting an example instrument access device.

FIG. 5 is a plan view schematically depicting instrument access device 500. In FIG. 5, instrument access device 500 includes envelope 502, three cannula ports 504 and one assistant port 506. As depicted in the example of FIG. 5, cannula ports 504 are positioned in a linear arrangement. In particular, in this example, the centers or central axes of cannula ports 504 are on a common circumferential line bisecting a generally spherical shaped envelope 502.

Figure 6:
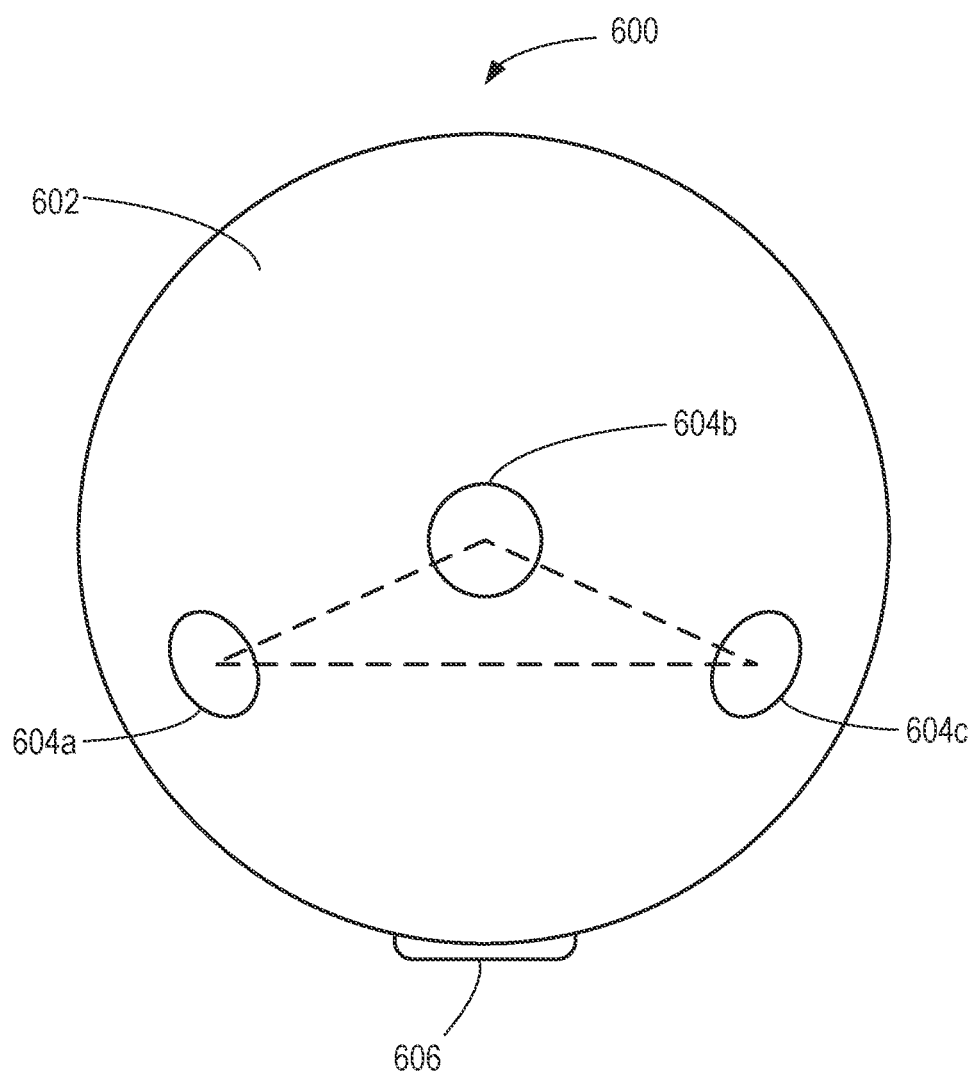
FIG. 6 is a plan view schematically depicting an example instrument access device.

FIG. 6 is a plan view schematically depicting instrument access device 600. In FIG. 6, instrument access device 600 includes envelope 602, three cannula ports collectively 604 and individually 604a-604c, and one assistant port 606. As depicted in the example of FIG. 6, cannula ports 604 are positioned in a triangular arrangement. In particular, in this example, the centers or central axes of two of cannula ports 604 are offset from the third cannula port in two directions. In an example, the center or central axis of cannula port 604a is offset from cannula port 604b in a first direction and a second direction, and the center or central axis of port 604c is offset from port 604b in a third direction and in the second direction. From the top view of FIG. 6, in particular, cannula port 604a is offset from cannula port 604b in a downward direction and in a leftward direction. Cannula port 604c is offset from cannula port 604b in the downward direction and in a rightward direction.

FIGS. 5 and 6 depict two example configurations of ports on an envelope of an instrument access device in accordance with this disclosure. In general, however, the ports of example instrument access devices may be optimally placed depending upon a number of variable surrounding the procedures in which such devices may be used. For example, the ports of example instrument access devices may be optimally placed depending upon the type of surgical procedure to be conducted with the device. Additionally or alternatively, the ports of example instrument access devices may be optimally placed depending upon the particular teleoperated surgical system employed in conjunction with the instrument access device.

Figure 7:
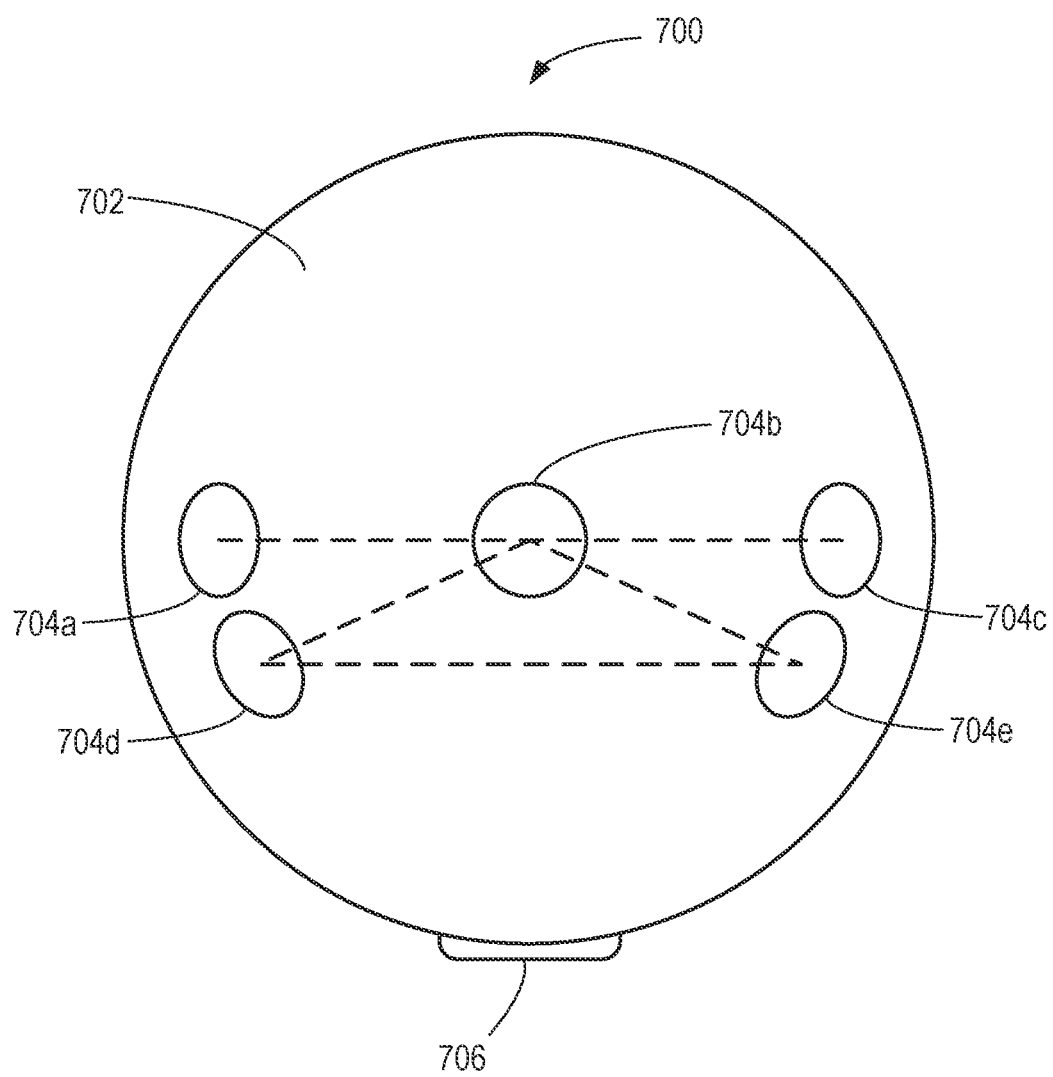
FIG. 7 is a plan view schematically depicting an example instrument access device.

FIG. 7 is a plan view schematically depicting instrument access device 700. In FIG. 7, instrument access device 700 includes envelope 702, five cannula ports 704 and one assistant port 706. In the example of FIG. 7, instrument access device 700 includes a first set of three cannula ports 704a, 704b, and 704c. Additionally, instrument access device 700 includes a second set of three cannula ports 704d, 704b, and 704e. In an example, instrument access device 700 is used in conjunction with a teleoperated surgical system including three teleoperated surgical instruments.

In total, instrument access device 700 includes five cannula ports 704, which is greater in number than the number of instruments included in the teleoperated surgical system. However, each of the first set of three cannula ports 704a, 704b, and 704c and the second set of three cannula ports 704d, 704b, and 704e is equal in number to the number of instruments. In this example, the first set of three cannula ports 704a, 704b, and 704c may be located on envelope 702 in accordance with a first type of surgical procedure, and the second set of three cannula ports 704d, 704b, and 704e may be located on envelope 702 in accordance with a second type of surgical procedure. Thus, increasing the range of application and flexibility of use of instrument access device 700.

FIGS. 8A-8E are elevation views schematically depicting a number of example instrument access devices with differently shaped envelopes. For simplicity, the example devices of FIGS. 8A-8E are depicted without cannula ports or assistant ports. However, as with other examples in accordance with this disclosure, each of these devices may include, for example, a plurality of ports coupled to the envelope, each port including a cannula seal, the seal being sized and shaped to seal an outer surface of a cannula and to fix a position of the cannula relative to the port and the envelope.

Figure 8A:
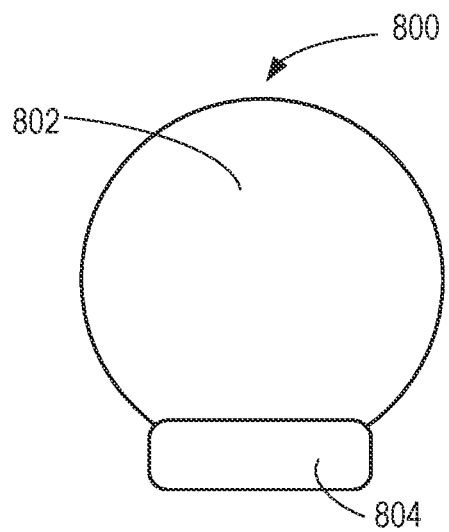
FIGS. 8A-8E are elevation views schematically depicting a number of example instrument access devices with differently shaped envelopes.

In FIG. 8A, instrument access device 800 includes envelope 802 and clamp 804. Envelope 802 includes a distal opening and a cavity. Clamp 804 is located in the distal opening of envelope 802. Envelope 802 can be a variety of shapes and sizes. In general, however, envelope 802, on condition that envelope 802 is pressurized with insufflation gas, extends radially outward beyond clamp 804. In the example of FIG. 8A, envelope 802 includes a spherical shape. Although not depicted in FIG. 8A, in examples, spherical envelope 802 may be formed from two semi-spherical sections, which are joined together at a seam or other junction.

Figure 8B:
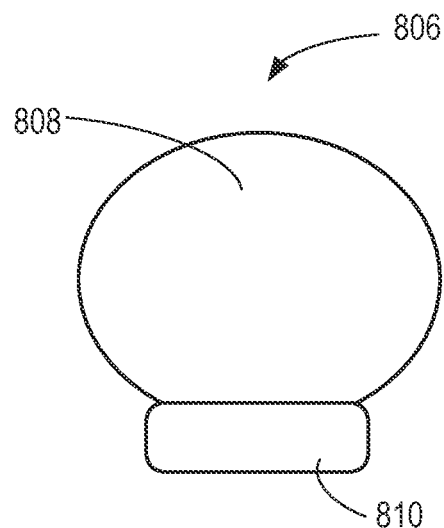

In FIG. 8B, instrument access device 806 includes envelope 808 and clamp 810. Envelope 808 includes a distal opening and a cavity. Clamp 810 is located in the distal opening of envelope 808. Envelope 808 can be a variety of shapes and sizes. In general, however, envelope 808, on condition that envelope 808 is pressurized with insufflation gas, extends radially outward beyond clamp 810. In the example of FIG. 8B, envelope 808 includes an oblate spherical shape. Although not depicted in FIG. 8B, in examples, oblate spherical envelope 808 may be formed from two semi-spherical sections, which are joined together at a seam or other junction.

Figure 8C:
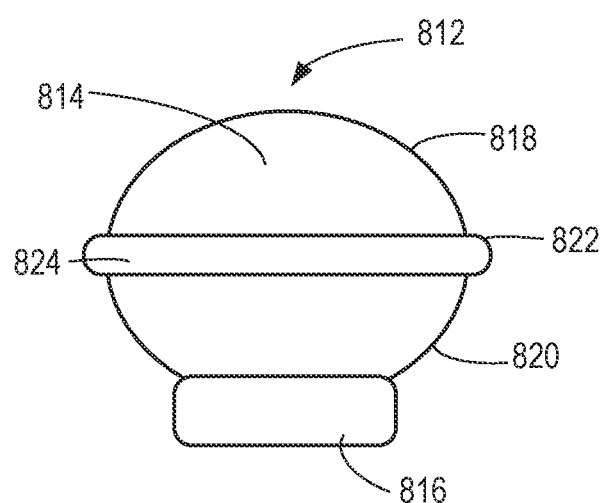

In FIG. 8C, instrument access device 812 includes envelope 814 and clamp 816. Envelope 814 includes a distal opening and a cavity. Clamp 816 is located in the distal opening of envelope 814. Envelope 814 can be a variety of shapes and sizes. In general, however, envelope 814, on condition that envelope 814 is pressurized with insufflation gas, extends radially outward beyond clamp 816. In the example of FIG. 8C, envelope 814 includes a lenticular shape. The lenticular shaped envelope 814 includes a first convex end 818, second convex end 820, and equatorial region 822. Second convex end 820 is generally opposed to/reverse of first convex end 818. Equatorial region 822 is between and joins first convex end 818 and second convex end 820. In the example of 8C, equatorial region 822 includes rib 824, which extends radially outward from first convex end 818 and second convex end 820. Lenticular shaped envelope 814 may be formed from two or more sections, which are joined together at seam(s) or other junction(s).

Figure 8D:
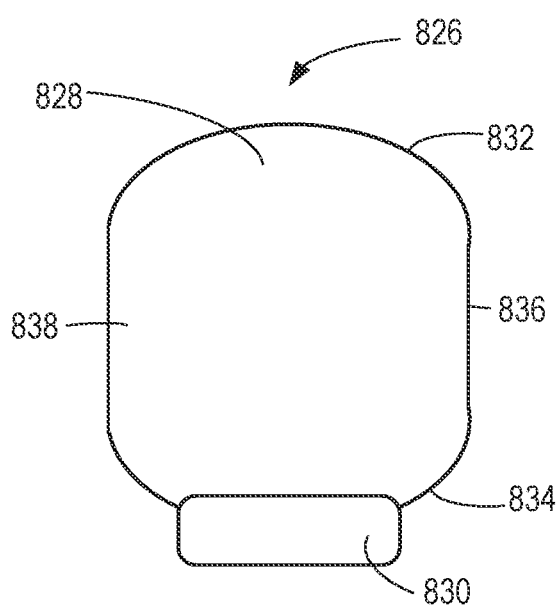

In FIG. 8D, instrument access device 826 includes envelope 828. Instrument access device 826 can be substantially similar to instrument access device 812 of FIG. 8C, except that lenticular shaped envelope 828 includes an elongated cylindrical equatorial region. For example, envelope 828, on condition that envelope 828 is pressurized with insufflation gas, extends radially outward beyond clamp 830. In the example of FIG. 8D, envelope 828 includes a lenticular shape. The lenticular shaped envelope 828 includes a first convex end 832, second convex end 834, and equatorial region 836. Second convex end 834 is generally opposed to/reverse of first convex end 832. Equatorial region 836 is between and joins first convex end 832 and second convex end 834. In the example of 8C, equatorial region 836 includes cylinder 838.

Figure 8E:
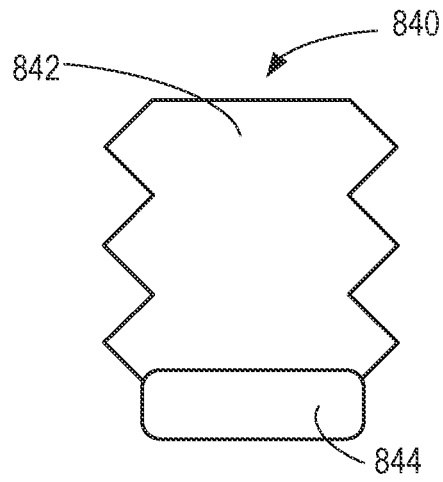

In FIG. 8E, instrument access device 840 includes envelope 842 and clamp 844. Envelope 842 includes a distal opening and a cavity. Clamp 844 is located in the distal opening of envelope 842. Envelope 842 can be a variety of shapes and sizes. In general, however, envelope 842, on condition that envelope 842 is pressurized with insufflation gas, extends radially outward beyond clamp 844. In the example of FIG. 8E, envelope 840 includes a bellows shape. Although not depicted in FIG. 8E, in examples, bellows shaped envelope 842 may be formed from two or more sections, which are joined together at seam(s) or other junction(s).

Envelopes 800, 806, 812, 826, and 840 of FIGS. 8A-8E can be manufactured from a variety of materials, including a variety of transparent polymers. In an example, envelopes 800, 806, 812, 826, and 840 are manufactured from a thermoplastic polyurethane (TPU). Envelopes 800, 806, 812, 826, and 840 can be manufactured in a variety of ways, including vacuum forming. In another example, envelopes 800, 806, 812, 826, and 840 are manufactured from a flat panel with multiple seams, which are joined to one another to form the final shape of the envelope.

Envelopes 800, 806, 812, 826, and 840 of FIGS. 8A-8E are examples of different shapes in which envelopes in accordance with this disclosure may be formed. The shapes represented in FIGS. 8A-8E are merely illustrative and are meant to describe the general shape of example envelopes; in practice, actual manufactured envelopes may vary slightly in shape. For example, a spherical envelope, when manufactured, may not be perfectly spherical but generally spherical or spheroid shaped. Additionally, the notion of certain geometrical shapes of envelopes in accordance with this disclosures includes variations of such shapes, for example, generally spherical includes spherical, spheroid, and oblate spheroid shapes. Additionally, other shapes not specifically illustrated are possible, including, for example, an ovoid shaped envelope.

Persons of skill in the art will understand that any of the features described above may be combined with any of the other example features, as long as the features are not mutually exclusive. All possible combinations of features are contemplated, depending on clinical or other design requirements. In addition, if manipulating system units are combined into a single system (e.g., telesurgery system), each individual unit may have the same configuration of features, or, one patient-side unit may have one configuration of features and another patient-side unit may have a second, different configuration of features.

The examples (e.g., methods, systems, or devices) described herein may be applicable to surgical procedures, non-surgical medical procedures, diagnostic procedures, cosmetic procedures, and non-medical procedures or applications. The examples may also be applicable for training, or for obtaining information, such as imaging procedures. The examples may be applicable to handling of tissue that has been removed from human or animal anatomies and will not be returned to a human or animal, or for use with human or animal cadavers. The examples may be used for industrial applications, general robotic uses, manipulation of non-tissue work pieces, as part of an artificial intelligence system, or in a transportation system.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. But, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A method of using an instrument access device of a teleoperated surgical system, the method comprising:
    attaching a clamp of the instrument access device to a wound retractor; and
    pressurizing an envelope of the instrument access device with insufflation gas to extend the envelope radially outward beyond an outward periphery of the clamp, wherein the envelope comprises:
        a distal opening in which the clamp is arranged; and
        a plurality of ports coupled to the envelope, each of the plurality of ports including a seal.
2. The method of claim 1 further comprising:
    inserting a first cannula in a first port of the plurality of ports, an outer surface of the first cannula sealing with a first seal of the first port and being fixed in position relative to the first port and the envelope.
3. The method of claim 2 further comprising:
    inserting a second cannula in a second port of the plurality of ports, an outer surface of the second cannula sealing with a second seal of the second port and being fixed in position relative to the second port and the envelope.
4. The method of claim 3 further comprising:
    inserting a first instrument into the first cannula and a second instrument into the second cannula.
5. The method of claim 4 further comprising:
    articulating a portion of the first instrument and a portion of the second instrument in the envelope and outside a body of a patient while a first end effector of the first instrument and a second end effector of the second instrument are located at or near a surface of the body in which the wound retractor is arranged.
6. The method claim 1, wherein:
    the plurality of ports are coupled to the envelope in a linear arrangement.
7. The method of claim 6, wherein:
    the envelope comprises a substantially spherical shape; and
    the plurality of ports are on a common circumferential line bisecting the spherical shaped envelope.
8. The method of claim 1, wherein:
    the plurality of ports comprises a first port, a second port, and a third port; and
    the first port, the second port, and the third port are coupled to the envelope in a triangular arrangement.
9. The method of claim 1, wherein:
    the plurality of ports comprise a first port and a second port;
    the first port comprises an aperture of a first size; and
    the second port comprises an aperture of a second size different from the first size.
10. The method of claim 1, wherein:
    one or more of the seals of the plurality of ports comprises an O-ring; and
    the O-ring is sized to seal against an outer surface of a cannula and to fix a position of the cannula relative to a port of the plurality of ports and the envelope.
11. The method of claim 1, wherein:
    one of the seals of the plurality of ports comprises a first seal and a second seal;
    the first seal is sized and shaped to seal against an outer surface of a cannula and to fix a position of the cannula relative to a port of the plurality of ports and the envelope; and
    the second seal is configured to seal against the outer surface of the cannula on a first condition that the cannula is received through the port and to seal the envelope on a second condition that the cannula is not received through the port.
12. The method of claim 11, wherein:
    the first seal comprises an O-ring; and
    the second seal comprises a slit seal.
13. A method of using an instrument access device of a teleoperated surgical system, the method comprising:
    attaching a clamp of the instrument access device to a wound retractor; and
    pressurizing an envelope of the instrument access device with insufflation gas to form a substantially spherical shape, wherein the envelope comprises:
        a distal opening in which the clamp is arranged; and
        a plurality of ports coupled to the envelope, each of the plurality of ports including a seal.
14. The method of claim 13 further comprising:
    inserting a first cannula in a first port of the plurality of ports, an outer surface of the first cannula sealing with a first seal of the first port and being fixed in position relative to the first port and the envelope.
15. The method of claim 14 further comprising:
    inserting a second cannula in a second port of the plurality of ports, an outer surface of the second cannula sealing with a second seal of the second port and being fixed in position relative to the second port and the envelope.
16. The method of claim 15 further comprising:
    inserting a first instrument into the first cannula and a second instrument into the second cannula.
17. The method of claim 16 further comprising:
    articulating a portion of the first instrument and a portion of the second instrument in the envelope and outside a body of a patient while a first end effector of the first instrument and a second end effector of the second instrument are located at or near a surface of the body in which the wound retractor is arranged.

18. The method of claim 13, wherein the plurality of ports are on a common circumferential line bisecting the spherical shaped envelope.

19. The method of claim 13, wherein:
one of the seals of the plurality of ports comprises a first seal and a second seal;
the first seal is sized and shaped to seal against an outer surface of a cannula and to fix a position of the cannula relative to a port of the plurality of ports and the envelope; and
the second seal is configured to seal against the outer surface of the cannula on a first condition that the cannula is received through the port and to seal the envelope on a second condition that the cannula is not received through the port.

20. The method of claim 19, wherein:
the first seal comprises an O-ring; and
the second seal comprises a slit seal.

\* \* \* \* \*